United States Patent [19]

Yannas

[11] Patent Number: 4,902,289

[45] Date of Patent: Feb. 20, 1990

[54] MULTILAYER BIOREPLACEABLE BLOOD VESSEL PROSTHESIS

[75] Inventor: Ioannis V. Yannas, Newton Center, Mass.

[73] Assignee: Massachusetts Institute of Technology, Cambridge, Mass.

[21] Appl. No.: 230,110

[22] Filed: Aug. 9, 1988

Related U.S. Application Data

[60] Division of Ser. No. 3,178, Jan. 12, 1987, Pat. No. 4,787,900, which is a continuation of Ser. No. 369,614, Apr. 19, 1982, abandoned.

[51] Int. Cl.$^4$ ............................................. A61F 1/24
[52] U.S. Cl. ........................................ 623/1; 623/66
[58] Field of Search .................. 623/1, 2, 10, 11, 16, 623/66

[56] References Cited

U.S. PATENT DOCUMENTS

| | | | |
|---|---|---|---|
| 4,252,759 | 2/1981 | Yannas et al. | 623/1 |
| 4,280,954 | 7/1981 | Yannas et al. | 623/1 |
| 4,286,341 | 9/1981 | Greer et al. | 623/1 |
| 4,522,753 | 6/1985 | Yannas et al. | 623/1 |
| 4,539,716 | 9/1985 | Bell | 623/1 |

FOREIGN PATENT DOCUMENTS

| | | | |
|---|---|---|---|
| 2255743 | 5/1973 | Fed. Rep. of Germany | 623/1 |

*Primary Examiner*—Richard J. Apley
*Assistant Examiner*—David J. Isabella
*Attorney, Agent, or Firm*—Paul J. Cook

[57] ABSTRACT

Process for forming a multilayer blood vessel prosthesis. Each layer is formed from bioreplaceable materials which include those produced by contacting collagen with an aminopolysaccharide and subsequently covalently crosslinking the resluting polymer, polymers of hydroxyacetic acid and the like. Cross flow filtration molding and wet extrusion molding are two processes which are particularly useful for forming the inner layer of the blood vessel prosthesis. The outer layer of the blood vessel prosthesis is preferably formed by freeze drying a dispersion of the bioreplaceable material onto the inner layer(s). The disclosed blood vessel prosthesis is a multilayer structure with each layer having a porosity and other physicochemical and mechanical characteristics selected to maximize the effectivenes of the blood vessel. The prosthesis funcitons initially as a thromboresistant conduit with mechanical properties which match those of the adjacent natural blood vessel. Eventually, the prosthesis functions as a regeneration template which is replaced by new connective tissue that forms during the healing process following attachment of the prosthesis.

16 Claims, No Drawings

MULTILAYER BIOREPLACEABLE BLOOD VESSEL PROSTHESIS

GOVERNMENT SPONSORSHIP

Work relating to this invention was partially supported by a contract from the National Institutes of Health, Contract/Grant No. 5 R01 HL24 036-02.

This is a divisional of co-pending application Ser. No. 003,178, filed on Jan. 12, 1987, now U.S. Pat. No. 4,787,900, which is a continuation of Ser. No. 369,614, filed on Apr. 19, 1982, now abandoned.

BACKGROUND OF THE INVENTION

It is widely acknowledged that the use of autologous vascular tissue in repair or replacement surgical procedures involving blood vessels, especially small blood vessels (i.e., 5 mm or less) provides long-term patency superior to that of commercially available prostheses. However, the use of autologous vascular grafts (eg. autologous vein grafts used in coronary bypass surgery) is associated with several problems. For example, harvesting of an autologous vascular graft constitutes a serious surgical invasion which occasionally leads to complications. Furthermore, the autologous vascular graft may frequently be unavailable due to specific morphological or pathophysiological characteristics of the individual patient. For example, a patient may lack a length of vein of the appropriate caliber or an existing disease (eg. varicose veins) may result in veins of unsuitable mechanical compliance. In addition to the foregoing, the use of autologous vein grafts for coronary bypass or femoropopliteal bypass or for interposed grafting of arteries frequently leads to development of intimal proliferation which eventually leads to loss of patency.

The experience with autologous vein grafts suggests the need for a suturable tubular product available without invading the patient. This product should be readily available in sterile form and in a large variety of calibers, degrees of taper of internal diameter and degrees of bifurcation (branching). In addition to ready availability and long-term patency, the graft should also remain free of aneurysms, infection and calcification and should not cause formation of emboli nor injure the components of blood over the duration of anticipated use.

The present invention is a blood vessel prosthesis which meets all of the foregoing criteria.

SUMMARY OF THE INVENTION

A blood vessel prosthesis in accordance with the present invention is a multilayer tubular structure with each layer being formed from a bioreplaceable material that is capable of being prepared in the form of a strong, suturable tubular conduit of complex geometry. This bioreplaceable material can be either a natural or a synthetic polymer. The preferred natural material is collagen-aminopolysaccharide. The preferred synthetic material is a polymer of hydroxyacetic acid. Adjacent layers can be prepared by use of different polymers giving a multilayered composite tubular structure.

The material of the blood vessel prosthesis is capable of undergoing biodegradation in a controlled fashion and replacement, without incidence of cellular proliferative processes, synthesis of fibrotic tissue or calcification. The use of the prosthesis of the present invention enables regeneration of the transected vascular wall of the host, thereby obviating long-term complications due to the presence of an artificial prosthesis. Of course, the material of the blood vessel is compatible with blood and does not cause platelet aggregation or activation of critical steps of the intrinsic and extrinsic coagulation cascades.

The multilayer tubular structure in accordance with the present invention possesses mechanical strength sufficient for convenient suturing and for withstanding without rupture the cyclical load pattern imposed on it by the cardiovascular system of which it forms a part. Its mechanical compliance matches the compliance of the blood vessel to which the graft is sutured, thereby minimizing thrombus formation caused by a geometric discontinuity (expansion or contraction of conduit). The prosthesis has sufficiently low porosity at the bloodgraft interface to prevent substantial leaking of whole blood or blood components. The blood compatibility is sufficient to prevent thrombosis or injury to blood components or generation of emboli over the period of time during which the graft is being replaced by regenerating vascular tissue.

The prosthesis has the property of replacing the vital functions of blood vessel both over a short-term period, up to about 4 weeks, in its intact or quasi-intact form; as well as the property of replacing the functions of a blood vessel over a long-term period, in excess of about 4 weeks, in its regenerated form, following a process of biological self-disposal and replacement by regenerating vascular tissue of the host. The long term function of the prosthesis is related to its ability to act as a tissue regeneration template, a biological mold which guides adjacent tissue of the blood vessel wall to regrow the segment which was removed by surgery. The term bioreplaceable refers to this process of biological self-disposal and replacement by regeneration.

Accordingly an object of the invention is to provide a blood vessel prosthesis which possesses many of the advantages of autologous vascular tissue and which can be used in place of autologous vascular grafts to eliminate many of the problems associated with their use.

A further object of the invention is to provide a process for making such a blood vessel prosthesis.

BRIEF DESCRIPTION OF THE DRAWINGS

FIG. 1 is a cross-sectional view of a blood vessel prosthesis in accordance with the present invention;

FIG. 2 is a diagrammatic illustration of the process of the present invention.

DESCRIPTION OF THE PREFERRED EMBODIMENTS

At the outset the invention is described in its broadest overall aspects with a more detailed description following. As is shown in FIG. 1, the blood vessel prosthesis 10 of the present invention is, in one important embodiment, a multilayer tubular structure consisting of an inner tubular layer 12 comprising a relatively smooth and non-porous bioreplaceable polymeric lining, optionally seeded with endothelial, smooth muscle or fibroblast cells prior to grafting, and which serves as a scaffold for neointimal and neomedial tissue generation; and, an outer tubular layer 14 comprising a tough and highly porous bioreplaceable polymeric layer optionally seeded with smooth muscle or fibroblast cells prior to grafting and which serves as a scaffold for neoadventitial and neomedial tissue generation and mechanical attachment of the graft to the host's perivascular tissues.

Following the complete disposal of the graft by biodegradation and its replacement by neovascular tissue without incidence of cellular proliferative processes, the newly formed blood vessel possesses the histological structure of the physiological blood vessel wall.

The preferred materials for the prosthesis of the present invention are cross-linked collagen-aminopolysaccharide composite materials disclosed in U.S. Pat. No. 4,280,954 by Yannas et al., the teachings of which are incorporated herein by reference.

These composite materials have a balance of mechanical, chemical and physiological properties which make them useful in surgical sutures and prostheses of controlled biodegradability (resorption) and controlled ability to prevent development of a foreign body reaction, and many are also useful in applications in which blood compatibility is required. Such materials are formed by intimately contacting collagen with an aminopolysaccharide under conditions at which they form a reaction product and subsequently covalently cross-linking the reaction product The products of such syntheses are collagen molecules or collagen fibrils with long aminopolysaccharide chains attached to them. Covalent cross-linking anchors the aminopolysaccharide chains to the collagen so that a significant residual quantity of aminopolysaccharide remains permanently bound to collagen even after washing in strong aminopolysaccharide solvents for several weeks.

Collagen can be reacted with an aminopolysaccharide in aqueous acidic solutions. Suitable collagen can be derived from a number of animal sources, either in the form of a solid powder or in the form of a dispersion, and suitable aminopolysaccharides include, but are not limited to chondroitin 4-sulfate chondroitin 6-sulfate, heparan sulfate dermatan sulfate, keratan sulfate, heparin, hyaluronic acid or chitosan. These reactions can be carried out at room temperature. Typically, small amounts of collagen, such as 0.3% by weight, are dispersed in a dilute acetic acid solution and thoroughly agitated. The polysaccharide is then slowly added, for example dropwise, into the aqueous collagen dispersion, which causes the coprecipitation of collagen and aminopolysaccharide. The coprecipitate is a tangled mass of collagen fibrils coated with aminopolysaccharide which somewhat resembles a tangled ball of yarn. This tangled mass of fibers can be homogenized to form a homogeneous dispersion of fine fibers and then filtered or extruded and dried.

The conditions for maximum attachment of aminopolysaccharide without significant partial denaturation (gelatinization) has been found to be a pH of about 3 and a temperature of about 37° C. Although these conditions are preferred, other reaction conditions which result in a significant reaction between collagen and aminopolysaccharide are also suitable.

Collagen and aminopolysaccharides can be reacted in many ways. The essential requirement is that the two materials be intimately contacted under conditions which allow the aminopolysaccharides to attach to the collagen chains. The collagen-aminopolysaccharide product prepared as described above can be formed into sheets, films, tubes and other shapes or articles for its ultimate application. In accordance with the present invention the collagen-aminopolysaccharide product is formed into tubes and thereafter is cross-linked.

Although the natural collagen-aminopolysaccharide polymer is the preferred material of the invention, other biodegradable and bioreplaceable materials, both natural and synthetic can be used. An example of a synthetic material useful in the invention is a polymer of hydroxacetic acid. Polyhydroxyacetic ester has suitable mechanical properties. Although polyhydroxyacetic ester eventually undergoes complete biodegradation when implanted, its short term strength makes it quite useful as a prosthetic device material.

One method for forming the inner conduit 12 is the cross-flow filtration molding process disclosed in U.S. Pat. No. 4,252,759 entitled "Cross Flow Filtration Molding Method", by Yannas, et al, the teachings of which are incorporated herein by reference. The molding apparatus includes a mold with porous walls having the predetermined shape. The porous walls contain pores having a size sufficient to retain dispersed particles on the wall surface as liquid medium passes through the walls. Means for introducing dispersion to the mold are also present, and typically comprise a pump for pumping dispersion through the mold. Means for applying hydrostatic pressure to dispersion in the porous mold are also part of the apparatus. Typically, such means for applying pressure might be a source of compressed gas attached to a reservoir for the dispersion. The reservoir and a flow development module to eliminate hydrodynamic end effects in the mold are optionally employed.

The cross flow filtration molding process comprises pumping a dispersion of particles through a mold having porous walls which allow transport of a portion of the dispersion medium therethrough. Hydrostatic pressure is applied to drive dispersion medium through the porous mold walls thereby causing particles to deposit on the mold walls to form an article having the predetermined shape. After sufficient particles have deposited to provide the shaped article with the wall thicknesses desired, the flow of dispersion through the mold is halted. If the dispersion used is the preferred collagen-aminopolysaccharide, the shaped article is cross-linked to provide it with significantly improved structural integrity.

The amount of hydrostatic pressure necessary to drive the dispersion through the porous mold walls will vary with many factors, including the chemical composition size, charge and concentration of particles; the chemical composition of the liquid medium; the shape, size, wall thickness, etc., of the article to be molded; and the size of pores in the mold walls. In the case of a dispersion of coprecipitated collagenaminopolysaccharide particles, for example, the pressure applied should be at least about ten p.s.i.g. to achieve a practical rate of medium transport through the mold walls. With larger particles, lower pressures can be used. Also, the desired pressure difference across the mold wall can be established by applying vacuum to the mold exterior.

The wall thickness of the tube produced in the mold can be varied. This is primarily done by adjusting the molding time, but other factors such as the dispersion flow rate, the hydrostatic pressure applied, the dispersion concentration, etc. also affect wall thickness. In accordance with the present invention the wall thickness of inner tube 12 is between the range of 0.1 to 5.0 mm.

It is clear, of course, that a wide variety of mold shapes besides hollow tubing could be employed. In fact, it is believed that the mold could be virtually any closed shape which has at least two ports. Thus, the mold might have the shape of an elbow, T-joint, bifurcated tubes, tubes with tapering diameters, or other shape. The fact that the mold can be virtually any shape is particularly beneficial since a great variety of morphology is found in natural blood vessels.

The incorporation of a woven or knitted fabric, e.g. a polyester velour or mesh, within the prosthesis of the invention serves to mechanically reinforce the prosthesis. One way to incorporate such a fabric within the prosthesis is to line the cross flow filtration mold with the fabric before pumping the dispersion of bioreplaceable particles through the mold.

Another method for forming a collagen-aminopolysaccharide inner conduit 12 is the wet extrusion molding process. In this process a collagen dispersion is extruded through a die over a mandrel into a precipitating aminopolysaccharide bath.

The preferred conditions for producing the collagen tubes by the wet extrusion process are a collagen concentration of 2.5% and a pressure of 12 p.s.i.g. for extrusion. Thickerwalled tubes may be produced uniformly at slightly higher collagen concentrations and extrusion pressures.

The wet extrusion molding process is suitable for fast production of the inner conduit but currently appears limited to fabrication of articles with axial symmetry, i.e., tubes, fibers or sheets. The cross flow filtration molding process, on the other hand, is relatively slow but is suitable for molding of hollow articles of narrow shapes, including bifurcated tubes and tubes with tapering diameters.

As seen in FIG. 2, after the initial formation of the preferred collagen-aminopolysaccharide inner conduit by either the wet extrusion method or the cross flow filtration method, it is cross-linked. If the inner conduit is formed from a synthetic bioreplaceable material, e.g., a polymer of hydroxyacetic acid, there is no cross-linking step, as the material degrades by hydrolysis. Covalent cross-linking can be achieved by many specific techniques with the general categories being chemical, radiation and dehydrothermal methods. An advantage to most cross-linking techniques contemplated, including glutaraldehyde cross-linking and dehydrothermal cross-linking, is that they also serve in removing bacterial growths from the materials. Thus, the composites are being sterilized at the same time that they are cross-linked.

One suitable chemical method for covalently cross-linking the collagen-aminopolysaccharide composite is known as aldehyde cross-linking. In this process the inner tube 12 is contacted with aqueous solutions of aldehyde, which serve to cross-link the materials. Suitable aldehydes include formaldehyde, glutaraldehyde and glyoxal. The preferred aldehyde is glutaraldehyde because it yields the desired level of cross-link density more rapidly than other aldehydes and is also capable of increasing the cross-link density to a relatively high level. It has been noted that immersing the preferred collagen-aminopolysaccharide composites in aldehyde solutions causes partial removal of the polysaccharide component by dissolution thereby lessening the amount of aminopolysaccharide in the final product.

Covalent cross-linking of the preferred collagen-aminopolysaccharide inner conduit serves to prevent dissolution of aminopolysaccharide in aqueous solutions thereby making inner tube 12 useful for surgical prostheses. Covalent cross-linking also serves another important function by contributing to raising the resistance to enzymatic resorption of these materials. The exact mechanism by which crosslinking increases the resistance to enzymatic degradation is not entirely clear. It is possible that cross-linking anchors the aminopolysaccharide units to sites on the collagen chain which would normally be attacked by collagenase. Another possible explanation is that crosslinking tightens up the network of collagen fibers and physically restricts the diffusion of enzymes capable of degrading collagen.

The mechanical properties of collagen-aminopolysaccharide networks are generally improved by crosslinking. Typically, the fracture stress and elongation to break are increased following a moderate crosslinking treatment. Maximal increases in fracture stress and elongation to break are attained if the molded tube is air dried to a moisture content o about 10%-wt. prior to immersion in an aqueous aldehyde crosslinking bath.

In accordance with the present invention, the cross-linked inner conduit 12 should have an $M_C$ (number average molecular weight between cross-links) of between about 2,000 to 12,000

Materials with $M_C$ values below about 2,000 or above about 12,000 suffer significant losses in their mechanical properties while also undergoing bioreplacement at a rate which is either too slow (low $M_C$) or a rate which is too fast (high $M_C$). Composites with an $M_C$ of between about 5,000 and about 10,000 appear to have the best balance of mechanical properties and of bioreplacement rate and so this is the preferred range of cross-linking for the inner conduit 12. Such properties must include low porosity (average pore diameter less than 10 microns). Thus the inner conduit should be permeable to low molecular weight constituents of blood, but should not allow leakage of whole blood.

If the inner conduit 12 is formed by cross flow filtration molding, a mandrel is inserted into the lumen of inner conduit 12 and is used to immerse conduit 12 into an aldehyde solution. The above described procedure of forming the inner tube by the cross flow filtration method and thereafter cross linking the tube itself may be repeated to build up an inner tube having a wall thickness of 0.1 to 5.0 mm. If the inner conduit 12 is formed by wet extrusion molding, the mandrel which is already situated in the lumen of inner conduit 12 is used to immerse conduit 12 into an aldehyde solution.

As seen in FIG. 2, after the desired wall thickness is achieved, the inner tube 12 is treated to provide it with outer layer 14, having a thickness of at least 1.0 mm. As has been set forth above, the outer layer 14 is also formed from bioreplaceable materials, preferably collagen-aminopolysaccharides. The outer layer 14 is applied to the inner layer 12 by a freeze drying process. In its broadest overall aspects, this process is performed by immersing the cross linked inner tube 12 in a pan 22 containing the appropriate bioreplaceable polymeric dispersion. As is shown in FIG. 2, the inner tub 12 is supported on a mandrel 38 and the inner tube 12 is covered with the dispersion 17 to form the outer layer of bioreplaceable material. The pan 22 itself is placed on the shelf of a freeze dryer which is maintained at $-20°$ C. or lower by mechanical refrigeration or other methods known to the art. Soon after making contact with the cold shelf surface, the bioreplaceable polymer dispersion freezes and the ice crystals formed thereby are sublimed in the vacuum provided by the freeze dryer.

Eventually, the dispersion is converted to a highly porous, spongy, solid mass which can be cut to almost any desired shape, i.e. elbow, bifurcated tubes, tapered cylinder, by use of an appropriate tool. By use of such a tool, the porous mass is fashioned to a cylinder which includes the inner layer and the mandrel.

If the outer layer of the conduit is made from collagen-aminopolysaccharides, then after the freeze dried slab is cut to the desired shape and wall thickness, the mandrel with the freeze dried conduit is subjected to temperature and vacuum conditions which lightly crosslink the multilayered structure, thereby preventing collapse of pores following immersion in aqueous media during subsequent processing or applications. This treatment also serves as a first sterilization step. Following such treatment, the conduit is further crosslinked, e.g., by immersing it in an aqueous glutaraldehyde bath. This process also serves as a second sterilization step. The conduit is then rinsed exhaustively in physiological saline to remove traces of unreacted glutaraldehyde.

The preferred collagen-aminopolysaccharide outer layer of the prothesis is biodegradable at a rate which can be controlled by adjusting the amount of aminopolysaccharide bonded to collagen and the density of crosslinks. The $M_C$ for this layer is between the range of 2,000 to 60,000 with 10,000-20,000 being the preferred range. Deviations from this range give nonoptimal biodegradation rates. The required mean pore diameter is 50 microns or greater.

Optional treatments of the formed multilayered conduit include (a) seedling of the inner or outer layers by inoculation with a suspension of endothelial cells, smooth muscle cells, or fibroblasts using a hypodermic syringe or other convenient seeding procedure; and (b) encasing the conduit in a tube fabricated from a woven or knitted fabric, e.g., a polyester velour or mesh. By seeding at certain loci, cell growth occurs rapidly in places where it would be delayed if allowed to occur naturally, thereby drastically reducing the amount of time necessary to regenerate the vascular tissue. Sheathing the conduit with fabric serves to provide a mechanical reinforcement for the conduit.

The mandrel, which the multilayered conduit is mounted on, is removed preferably following the above optional processing steps and prior to storage of the sterile conduit in a container. Just prior to use, the conduit is removed from its sterile environment and used surgically as a vascular bypass, as an interposed graft or as a patch graft for the blood vessel wall.

To be suitable for vascular prostheses, vessels 10 must have certain minimum mechanical properties. These are mechanical properties which would allow the suturing of candidate vessels sections of natural vessel, a process known as anastomosis. During suturing, such vascular (blood vessel) grafts must not tear as a result of the tensile forces applied to them by the suture nor should they tear when the suture is knotted. Suturability of vascular grafts, i.e., the ability of grafts to resist tearing while being sutured, is related to the intrinsic mechanical strength of the material, the thickness of the graft, the tension applied to the suture, and the rate at which the knot is pulled closed. Experimentation performed indicates that the minimum mechanical requirements for suturing a graft of at least 0.01 inches in thickness are: (1) an ultimate tensile strength at least 50 psi; and (2) an elongation at break of at least 10%.

The best materials for vascular prostheses should duplicate as closely as possible the mechanical behavior of natural vessels. The most stringent physiological loading conditions occur in the elastic arteries, such as the aorta, where fatigue can occur as a result of blood pressure fluctuations associated with the systole-diastole cycle. The static mechanical properties of the thoracic aorta can be used as a mechanical model. The stress-strain curve of the thoracic aorta in the longitudinal direction of persons 20-29 years of age has been determined by Yamada. See Yamada, H., "Strength of Biological Materials", ed. F. G. Evans, Chapter 4, Williams & Wilkins (1970). From this plot, the mechanical properties were calculated and found to be: (1) an ultimate tensile strength of 360 psi; (2) elongation at break of 85%; (3) tangent modulus at 1% elongation of 50 psi; and (4) fracture work, i.e., the work to rupture (a measure of toughness), of 21,000 psi-%. These four mechanical properties serve as a quantitative standard for mechanical properties of vascular prostheses.

The process of the present invention is further illustrated by the following non-limiting examples.

EXAMPLE 1

The raw material for molding gas a bovine hide collagen/chondroitin 6-sulfate dispersion prepared as follows: Three grams of glacial acetic acid were diluted into a volume of 1.0 liter with distilled, deionized water to give a 0.05 M solution of acetic acid. The fibrous, freeze-dried bovine hide collagen preparation was ground in a Wiley Mill, using a 20-mesh screen while cooling with liquid nitrogen.

An Eberbach jacketed blender was precooled by circulating cold water (0°-4° C.) through the jacket. Two hundred milliliters (ml) of 0.05 M acetic acid were transferred to the blender and 0.55 g of milled collagen was added to the blender contents. The collagen dispersion was stirred in the blender at high speed over 1 hr.

A solution of chondroitin 6-sulfate was prepared by dissolving 0.044 g of the aminopolysaccharide in 20 ml of 0.05 M acetic acid to make a 8%-wt. solution (dry collagen basis). The solution of aminopolysaccharide was added dropwise over a period of 5 min to the collagen dispersion while the latter was being stirred at high speed in the blender. After 15 min of additional stirring the dispersion was stored in a refrigerator until ready for use.

The total amount of collagen-chondroitin 6-sulfate dispersion used was first treated in a blender and then fed into an air-pressurized Plexiglas tank. A magnetic stirrer bar served to minimize particle concentration gradients inside the vessel. Dispersion exited from the bottom of the pressure vessel and flowed into a flow development module and perforated aluminum tube split lengthwise which acted as a mold for tubes. Filter paper was carefully glued to each of the two halves of the aluminum tubes using alpha cyanoacrylate adhesive The flow development module and mold had an inside diameter of 0.25 inches and the flow development module was 17 in. lorg whereas the mold was 10.5 in. long. Additionally, the perforated aluminum tubing had a series of 0.03" pores extending linearly every 45" of circumference and positioned every 0.01".

Upon entry into the tubular mold, a fraction of the water of the dispersion was forced through the filter paper and subsequently through the perforation in the tube wall where it evaporated into the atmosphere giving the outside of the mold a "sweating" appearance.

While transport of a fraction of water and particles proceeded radially inside the tube mold, the decanted bulk of the dispersion inside the mold flowed uneventfully in the axial direction and was pumped back to the pressure vessel through a dispersion return line where it was stirred and recycled back into the mold.

At an applied pressure of 30 psig, and a flow rate of approximately 2.5 ml/min, a gel layer of about 0.004 inches thick had formed after a period of about 6 hours of operation which, when air dried after decanting the non-gelled fluid, was sufficiently concentrated to be handled without loss of shape. Tubes fabricated in this manner were removed from the tubular mold without being detached from the filter paper and were subjected to an insolubilization (crosslinking) treatment by immersion in 250 ml. of 0.5% w/w glutaraldehyde solution for 8 hours. The 10-inch tube obtained has a thickness of 0.0028, 0.0030, 0.0034, 0.0034 and 0.0034 inches at distances of 2, 4, 6, 8 and 10 inches, respectively, from the upstream end of the tube.

The tube was mounted on a cylindrical Plexiglas mandrel, 0.0030 inches diameter, and was immersed in the pan of a freeze dryer containing a volume of collagen-aminopolysacharide dispersion which was sufficient to cover the tube completely. The ends of the mandrel rested on supports mounted on the pan. In this manner, the side of the tube closest to the bottom of the pan was prevented from contacting the latter.

The pan was placed on the shelf of a Virtis freeze dryer. The shelf had been precooled at −40° C. or lower by mechanical refrigeration. The chamber of the freeze dryer was closed tightly and a vacuum of 120 mTorr was established in the chamber. Several minutes after contact with the shelf, the dispersion solidified into a frozen slab which was marked by the characteristic pattern of ice crystals. The temperature of the shelf was increased to 0° C. Several hours later, the temperature of the shelf was slowly raised to 22° C. and the contents of the pan were removed in the form of a spongy, white solid slab. A specimen cut from the slab was examined in a scanning electron microscope revealing a mean pore diameter of about 80 m.

By use of a sharp tool, sufficient solid material was removed from the porous slab to expose the cylinder enclosed in the mass. A layer, approximately 1 mm thick, of porous material was left attached on the inner nonporous cylinder. The mandrel with the multilayered conduit was then placed in a vacuum oven where it was treated at 105° C. and 50 mTorr pressure over 24 hours. Following removal from the oven, the mandrel was placed in 250 ml of 0.5% w/w glutaraldehyde solution over 8 hours where it was additionally crosslinked and sterilized before being rinsed in sterile physiological saline over 24 hours to remove traces of unreacted glutaraldehyde. After removing the mandrel the multilayered conduit was stored either in 70/30 isopropanol water in a sterile container or was stored in the freeze-dried state inside a sterile container.

EXAMPLE 2

Example 1 was repeated except that 20%-wt. (dry collagen basis) of elastin was added to the collagen dispersion just before adding the mucopolysaccharide solution. Elastin was added to improve the mechanical behavior of the prosthesis by increasing the elongation to break. Elastin powder from bovine neck ligament (Sigma Chemical Co.) or Crolastin, Hydrolysed Elastin, MW 4,000 (Croda Ic., New York) were used.

EXAMPLE 3

Example 1 was repeated except that the mold used during cross flow filtration was much smaller in internal diameter, resulting in tubes with internal diameter of 2.6 mm and thickness 0.1 mm. The pressure level used to fabricate this tube was 100 psig, rather than 30 psig used in Example 1, and the total molding time was 2 hours or less under these conditions. The tubes formed thereby had a fracture stress of 200 psi and an elongation to break of 15%.

EXAMPLE 4

Example 4 was repeated except that a dispersion of endothelial cells from a canine vein was prepared according to the method of Ford et al. (J. W. Ford, W. E. Burkel and R. H. Kahn, Isolation of Adult Canine venous Endothelium for Tissue Culture, In vitro 17, 44, 1981). The cell dispersion was then inoculated into the inner layer of a multilayer conduit by use of a sterile hypodermic syringe. During inoculation the conduit was immersed in physiological saline maintained at 37° C.

I claim:

1. A multilayer blood vessel prosthesis comprising: a first inner conduit defining a relatively smooth walled lumen, said inner layer is crosslinked aminopolysacchride ride having a mean pore diameter below 10 microns, a wall thickness between 0.1 to 5.0 mm, and a number average molecular weight between crosslinks of between 2000 and 12,000 daltons and a second outer layer on said first layer, said outer layer formed a crosslinked freeze dried collagen-aminopolysascharide polymer having a mean pore diameter of at least 50 microns and a thickness of at least 1.0 mm.

2. The blood vessel prosthesis as set forth in claim 1 wherein the collagen-aminopolysaccharide comprises from 1 to 15% aminopolysaccharide.

3. The blood vessel prosthesis as set forth in claim 1 wherein the aminopolysaccharide is selected from a number of the group consisting of chondroitin-4-sulfate, chondroitin 6-sulfate, heparin sulfate, dermatan sulfate, keratan sulfate, heparin, hyalurenic acid and chitosan.

4. The blood vessel prosthesis as set forth in claim 1 wherein the outer layer has been crosslinked to an average molecular weight between cross-links of between 2,000 to 60,000.

5. The blood vessel prosthesis as set forth in claim 1 wherein the prosthesis has a tubular shape.

6. The blood vessel prosthesis as set forth in claim 1 wherein the prosthesis has a bifurcated tubular shape.

7. The blood vessel prosthesis as set forth in claim 1 wherein the prosthesis has a tapered cylinder shape 8. The blood vessel prosthesis as set forth in claim 1 wherein said inner layer is seeded with cells.

9. The blood vessel prosthesis as set forth in claim 8 wherein said inner layer is seeded with endothelial cells.

10. The blood vessel prosthesis as set forth in claim 8 wherein said inner layer is seeded with smooth muscle cells.

11. The blood vessel prosthesis as set forth in claim 10 wherein said inner layer is seeded with fibroblasts.

12. The blood vessel prosthesis as set forth in claim 1 wherein said outer layer is seeded with cells.

13. The blood vessel prosthesis as set forth in claim 12 wherein said outer layer is seeded with smooth muscle cells.

14. The blood vessel prosthesis as set forth in claim 12 wherein said outer layer is seeded with fibroblasts.

15. The blood vessel prosthesis as set forth in claim 1 wherein the prosthesis is sheathed with a woven or knitted fabric.

16. The blood vessel prosthesis as set forth in claim 1 wherein the prosthesis has incorporated within it a woven or knitted fabric.

* * * * *